United States Patent
Zhu

(10) Patent No.: US 8,653,095 B2
(45) Date of Patent: Feb. 18, 2014

(54) SMALL MOLECULES WITH ANTIMALARIAL ACTIVITY

(75) Inventor: Shuren Zhu, Potomac, MD (US)

(73) Assignee: Radix Pharmaceuticals, Inc., Potomac, MD (US)

( * ) Notice: Subject to any disclaimer, the term of this patent is extended or adjusted under 35 U.S.C. 154(b) by 286 days.

(21) Appl. No.: 13/135,868

(22) Filed: Jul. 18, 2011

(65) Prior Publication Data

US 2013/0023552 A1    Jan. 24, 2013

(51) Int. Cl.
*A61K 31/4375*    (2006.01)

(52) U.S. Cl.
USPC .......................... 514/279; 514/280

(58) Field of Classification Search
USPC ................................. 514/279, 280
See application file for complete search history.

(56) References Cited

U.S. PATENT DOCUMENTS 7,851,508 B2 * 12/2010 Zhu ............................ 514/579

OTHER PUBLICATIONS

Singh et al.; "In Vivo Anti-Malarial Evaluation of Ocimum Sanctum Linn. and O. Basilicum Linn."; 2010; Canadian Journal of Pure & Applied Sciences; 4(1): 1033-1037.*

* cited by examiner

*Primary Examiner* — Timothy Thomas

(57) ABSTRACT

The present invention provides new chemical compositions with desirable biological activity and toxicity profiles for the enhanced treatment of malaria.

1 Claim, 2 Drawing Sheets

Chemical structure of natural product derivatives (Formula B and Formula C).

Formula B

Formula C

Figure 1. Chemical structure of isolated natural product. (Formula A).
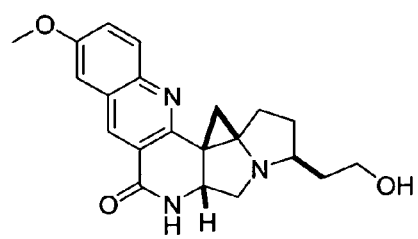
Formula A
Figure 2. Chemical structure of natural product derivatives (Formula B and Formula C).
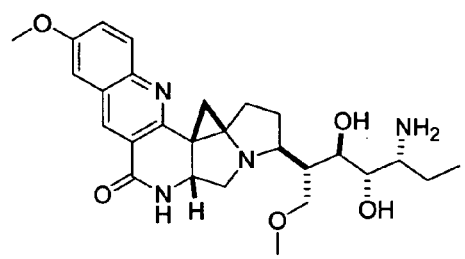 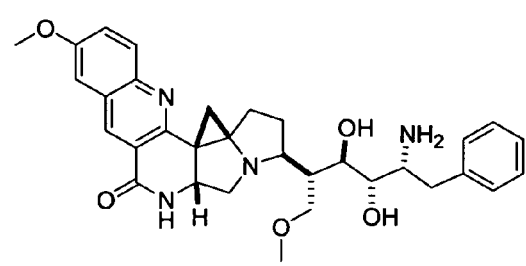
Formula B                    Formula C Figure 3. Synthesis of natural product derivatives Formula B and Formula C.
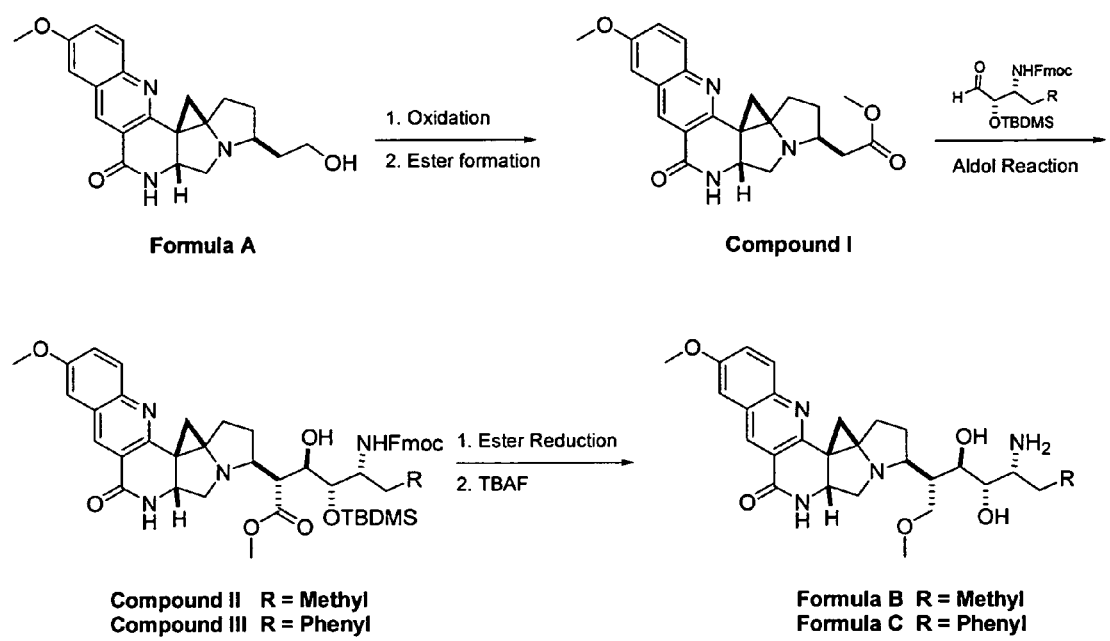

SMALL MOLECULES WITH ANTIMALARIAL ACTIVITY

STATEMENT REGARDING FEDERALLY SPONSORED RESEARCH OR DEVELOPMENT

This invention was supported by Public Health Service Grant Number: 2R44A/077109-03 for Radix Pharmaceuticals, Inc. The U.S. Government has a paid-up license in this invention and the right in limited circumstances to require the patent owner to license others on reasonable terms as provided for by the terms of Grant Number: 2R44/A077109-03 awarded by Public Health Service.

CROSS-REFERENCE TO RELATED APPLICATIONS

Not Applicable.

REFERENCE TO SEQUENCE LISTING, A TABLE, OR A COMPUTER PROGRAM LISTING COMPACT DISC APPENDIX

Not Applicable.

FIELD OF INVENTION

The present invention relates to new chemical compositions that are effective for the treatment of malaria.

BACKGROUND OF THE INVENTION

Malaria is the best known protozoal disease, caused by one of four species of the sporazoa type—*Plasmodium falciparum, P. vivax, P. ovale*, and *P. malariae*. It is one of the most common infectious diseases in at least 100 tropical and subtropical countries in Africa, Southeast Asia, and South America. According to WHO, one out of every seventeen people alive today will die from a disease transmitted by the bite of a mosquito. Worldwide, malaria infects 300-600 million people and kills about three million in a year. The increasing prevalence of multiple drug resistant strains of *Plasmodium falciparum* in most malaria endemic areas has significantly reduced the efficacy of current anti-malarial drugs for prophylaxis and treatment of this disease. Although drug resistance is a common problem in the treatment of most microbial infections, malaria and many neoplasms, the impact is more acute for malaria chemotherapy because of the limited number of clinically useful anti-malarial drugs.

Only six prescription drugs are available in the US for treating and/or preventing malaria: Atovaquone/proguanil, Doxycycline, Mefloquine, Primaquine, Chloroquine phosphate, and Hydroxychloroquine sulfate. All of them are discovered more than 40 years ago. Serious side effects are common. Primaquine is the only available causal prophylactics. It has a low therapeutic index. The use of chloroquine is limited because of the worldwide emergence of drug-resistant strains of *P. falciparum* and *P. vivax*. Proguanil has a short half-life and strains of *P. falciparum* resistant to proguanil are common. The newest antimalarial drug Mefloquine was developed in the late 1960s. It is initially reserved by WHO for use in regions where drug resistance to chloroquine is a serious problem. However, problems have arisen with mefloquine use. The cure rate for mefloquine-sulfadoxine-pyrimethamine treatment of *P. falciparum* in Southeast Asia fell from 96% in 1985 to as low as 50% in 1990. Mefloquine can also produce adverse neurological and psychiatric reactions.

Artemisinin and its derivatives are currently under development. However, these compounds cannot be used during pregnancy since they have shown fetotoxicity in rodent models. The current generations of artemisinins possess poor efficacy of monotherapy. Artemisinins do not interfere with hepatic stages of parasite development and therefore have no causal prophylactic value.

Therefore, novel medicinal agents are urgently needed to overcome the emergence of resistance and to control an ever-increasing number of epidemics caused by the malaria parasite.

For decades, natural products have been a wellspring of drugs and drug leads. According to a recent survey, 61% of the 877 small-molecule new chemical entities introduced as drugs worldwide during 1981-2002 can be traced to or were inspired by natural products. These include natural products (6%), natural product derivatives (27%), synthetic compounds with natural-product-derived pharmacophores (5%), and synthetic compounds designed on the basis of knowledge gained from a natural product (that is, a natural product mimic; 23%). In certain therapeutic areas, the productivity is higher: 78% of antibacterials and 74% of anticancer compounds are natural products or have been derived from, or inspired by, a natural product.

*Ocimum sanctum*, popularly known as Tulsi in Hindi and Holy Basil in English, is ubiquitous in Hindu tradition. In traditional Ayurvedic system of medicine, several medicinal properties have been attributed to this plant. Essential oil of Tulsi has antibacterial, antifungal and antiviral properties. It inhibits the growth of *E. coli, B. anthracis, M. tuberculosis*. Extracts from the plant have been found to possess anti-diabetic, antistress/adaptogenic, as well as antiallergic and immunomodulator effects. A variety of biologically active compounds have been isolated from the leaves, barks, roots and seeds of *Ocimum sanctum*. Those compounds include but are not limited to the following: eugenol, carvacrol, caryophyllene, ursolic acid, apigenin, luteolin, orientin, molludistin, vicenin, cirsilineol, cirsimaritin, isothymusin, etc. Trials have shown excellent antimalarial activity of *Ocimum sanctum*. Ayurvedic preparations containing *Ocimum sanctum, Allium stivum, Piper nigram* and *Curcuma longa* has been shown to possess antimalarial activity against *Plasmodium vivax* and *Plasmodium falciparum*. As far as its antimalarial effect is concerned essential oil of *Ocimum sanctum* has also been found to possess insecticidal and larvicidal activities against mosquitoes.

An ethanol extract of the dried root barks of *Ocimum sanctum* exhibited considerable in vitro antimalarial activity to warrant fractionation. On the basis of the initial activity of crude extracts, attention was focused on the bioactivity-guided fractionation of the EtOH extract of the dried barks, which resulted in the isolation of one new antimalarial natural product, Formula A. Its chemical structure is shown in FIG. 1. Two derivative compounds, Formula B and Formula C, were then synthesized from the original natural product Formula A. These derivative compounds are orally active against both sensitive and multidrug resistant malaria strains and possess good therapeutic indices. The chemical structures of the natural product derivatives, Formula B and Formula C, are shown in FIG. 2. The synthesis route is shown in FIG. 3.

Derivative compounds (Formula B and Formula C) underwent biological assessment against six strains of *P. falciparum*. These compounds exhibited superior and equally potent antimalarial activity against chloroquine sensitive and resistant malaria strains.

In mice models, both Formula B and Formula C have shown excellent blood schizonticidal activity and oral prophylactic activity. Mouse model studies also indicate that new compounds are much less toxic than existing antimalarial drugs (chloroquine, mefloquine and artemisinin derivatives) and are expected to possess wide therapeutic windows.

The present invention relates to new, more active and less toxic natural product derivatives for the treatment of malaria.

SUMMARY OF THE INVENTION

The present invention provides new chemical compositions and methods of isolation and synthesis and using as antimalarial agents thereof. The present invention relates to improvements in the chemotherapy of malaria through isolation and chemical synthesis of new compounds with desirable biological activity and toxicity profiles for enhanced treatment.

Accordingly, this invention provides new chemical compound Formula B, whose chemical structure is shown in FIG. 2.

Formula B

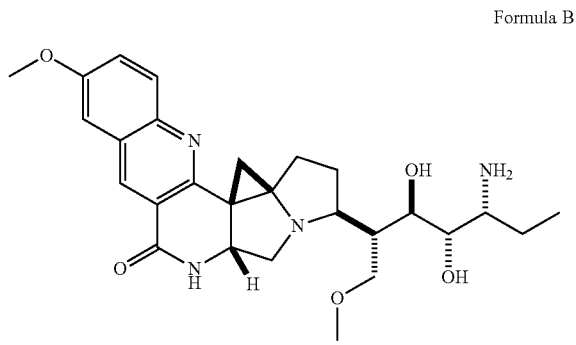

The invention also provides new chemical compound Formula C, whose chemical structure is shown in FIG. 2.

Formula C

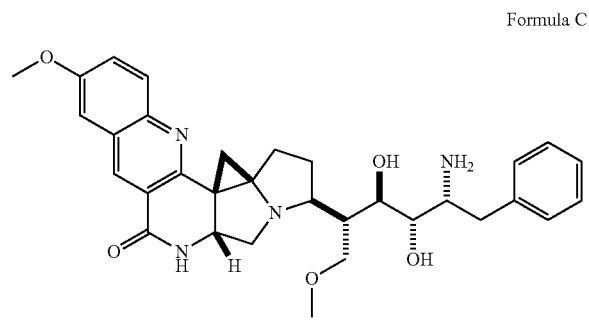

One natural product compound was isolated and purified from the plant *Ocimum sanctum* L. and two derivative compounds were synthesized. In vitro and in vivo antimalarial activities were evaluated. Natural product (Formula A) showed modest inhibitory activity against both chloroquine sensitive and chloroquine resistant malaria strains. The two natural product derivatives (Formula B and Formula C) showed equally effective and potent inhibitory activity against both chloroquine sensitive and chloroquine resistant malaria strains. It was observed that these derivative compounds possessed potent antimalarial activity in mouse malaria models. Hence, the present invention comprises the use of new chemical compounds for the enhanced treatment of malarial infections.

BRIEF DESCRIPTION OF THE DRAWINGS

These and other features, aspects, and advantages of the present invention will become better understood with regard to the following description and accompanying drawings wherein:

FIG. 1 shows the structures of isolated natural product compound Formula A.

FIG. 2 shows the structures of newly synthesized derivative compounds Formula B and Formula C.

FIG. 3 shows the chemical synthesis route.

DETAILED DESCRIPTION OF THE INVENTION

As mentioned earlier, the invention provides the following compounds: Formula B and Formula C, as shown in FIG. 2.

The invention is inclusive of the compounds described herein in any of their pharmaceutically acceptable forms, including isomers such as diastereomers and enantiomers, salts, solvates, polymorphs, and the like.

Isolation of Natural Product Formula A.

General Experimental Procedures. Melting points (uncorrected) were recorded on an Electrothermal 9100 instrument. Optical rotations were measured using a JASCO DIP-370 digital polarimeter in MeOH at ambient temperature. UV spectra were obtained in MeOH, using a Hewlett-Packard 8452A spectrophotometer. IR spectra were taken as KBr disks on an Ati Mattson (Genesis Series) FTIR spectrophotometer. The NMR spectra were recorded on a Bruker Avance DRX-500 instrument at 500 MHz ($^1$H) and 125 MHz ($^{13}$C) in appropriate deuteriated solvent. Multiplicity determinations (DEPT) and 2D NMR spectra (COSY, HMQC, HMBC) were run using standard Bruker pulse programs. The HRMS were obtained by direct injection using Bruker Bioapex-FTMS with electrospray ionization (ESI). TLC was carried out on Silica gel F254 plates, with appropriate solvent system. For flash column chromatography, Silica gel from J. T. Baker (40 µm flash) was used. Centrifugal preparative TLC (using a Chromatotron instrument, Harrison Research Inc. model 8924) was carried out on 4 mm Silica gel GF Chromatotron rotors (Analtech, Inc.), with the appropriate solvent system. The isolated compounds were visualized using UV light, followed by spraying with anisaldehyde/$H_2SO_4$ reagent. All solvents are recycled when possible.

Extraction and Isolation. The powdered dried root barks of *Ocimum sanctum* L. (10 kg) were extracted by percolation with 95% EtOH (18 L×3). The combined extracts were evaporated separately under reduced pressure and then freeze-dried to yield a thick paste (1.2 kg). The paste was then extracted with 0.05 N hydrochloric acid; the acid solution was extracted with chloroform. The chloroform was recycled and the residue from the chloroform solution was discarded. The aqueous phase was then made basic with sodium carbonate and extracted exhaustively with chloroform. The combined $CHCl_3$ fraction was dried over anhydrous $Na_2SO_4$ and evaporated under a vacuum to yield 482 g of residue. This $CHCl_3$ residue was flash chromatographed on silica gel, using $CHCl_3$—MeOH—$NH_4OH$ (95.75/4.0/0.25) as eluant to afford natural product Formula A as a pale yellow solid (34 g). Other natural products were also isolated. Recrystallization from $CHCl_3$—MeOH by slow evaporation at room temperature furnishes Formula A as pale yellow needles (27 g). Yield: 0.27% from dried root barks. The structure of Formula A is elucidated by MS (HRESIMS), IR, UV, and NMR (2D COSY, HMQC, HMBC) methods. New compound possesses satisfactory spectroscopic and analytical data.

Synthesis of Derivative Compounds Formula B and Formula C.

Synthesis of Compound I. Natural product Formula A (185 g) was dissolved in a mixture of $H_2O$ (500 mL) and $CH_3CN$ (500 mL). Chromium (VI) oxide ($CrO_3$, 5.1 g) and periodic acid ($H_5IO_6$, 233 g) were slowly added in. The resulting mixture was stirred vigorously for 8 hours at ambient temperature. Solvent was removed under reduced pressure. The slurry was treated with $CH_3CN$ (300 mL), and solid was filtered and discarded. The solution was concentrated to give a thick paste. This paste was dissolved in DMF (200 mL). Potassium carbonate (145 g) and methyl iodide (70 g) was slowly added in. The resulting mixture was stirred for 4 hours at ambient temperature. Solvent was removed under reduced pressure. The slurry was treated with $CHCl_3$ (300 mL), and solid was filtered and discarded. The solution was concentrated. This $CHCl_3$ residue was flash chromatographed on silica gel, using $CHCl_3$—MeOH—$NH_4OH$ (96.75/3.0/0.25) as eluant to afford compound I as a pale yellow solid (154 g, yield: 77%).

Synthesis of Compound II. Compound I (76 g) was dissolved in 200 mL of anhydrous THF. It was cooled to −78° C. Lithium diisopropylamide solution (2.0M in THF/heptanes, 193 mL) was slowly added. The resulting mixture was kept at −78° C. for 30 minutes. A solution of the corresponding aldehyde ([2-(tert-Butyl-dimethyl-silanyloxy)-1-ethyl-3-oxo-propyl]-carbamic acid 9H-fluoren-9-ylmethyl ester, 88 g) in 75 mL of THF was slowly added in while stirring at −78° C. After 2 hours, the reaction was quenched by slow addition of aqueous sodium bicarbonate (50 mL). The resulting mixture was concentrated to about 150 mL in volume and then partitioned between $CHCl_3$ and $H_2O$. The organic layer was separated, washed with brine, dried over anhydrous sodium sulfate, and concentrated. Flash chromatography on silica gel, using $CHCl_3$—MeOH—$NH_4OH$ (98.75/1.0/0.25) as eluant, afforded compound II as a white solid (133 g, yield: 81%).

Synthesis of Compound III. The synthesis of Compound III follows the same protocol as the synthesis of Compound II. A different aldehyde ([1-Benzyl-2-(tert-butyl-dimethyl-silanyloxy)-3-oxo-propyl]-carbamic acid 9H-fluoren-9-ylmethyl ester) was used. Compound III is a white solid. Yield: 84%.

Synthesis of Formula B. Compound II (131 g) was dissolved in toluene (500 mL). Lawesson reagent (125 g) was added in. The solution was heated at reflux for 4 hours. Solvent was then removed. The resulting mixture was partitioned between $CHCl_3$ and $H_2O$. The organic layer was separated, washed with brine, dried over anhydrous sodium sulfate, and concentrated. Flash chromatography on silica gel, using $CHCl_3$—MeOH—$NH_4OH$ (98.75/1.0/0.25) as eluant, afforded the thiono ester. The reduction of this thiono ester to corresponding ether was catalyzed by Raney® nickel under hydrogen atmosphere (50-60 psi). Following isolation, the ether was dissolved in DMF (200 mL), and tetrabutylammonium fluoride (81 g)) was added in. After 3 hours, solvent was removed under reduced pressure in a rotary evaporator. The residue was partitioned between ethyl acetate (500 mL) and water (500 mL). The organic layer was separated, washed with brine, and concentrated. Flash chromatography on silica gel, using $CHCl_3$—MeOH—$NH_4OH$ (97.75/2.0/0.25) as eluant, afforded Formula B as pale yellow solid. Crystallization from $CHCl_3$—MeOH by slow evaporation at room temperature gave Formula B as pale yellow needles (55 g). Yield: 71%.

Synthesis of Formula C. The synthesis of Formula C follows the same protocol as the synthesis of Formula B. Crystallization affords Formula C as pale yellow needles. Yield: 73%.

The structures of Formula B and Formula C are elucidated by MS (HRESIMS), IR, UV, and NMR (2D COSY, HMQC, HMBC) methods. Both compounds possess satisfactory spectroscopic and analytical data.

Formula B (hydrochloride salt): pale yellow needles, melting point 187-188° C.; $[\alpha]_D$ −22.9° (c 0.27, MeOH). $^1$H NMR ($CD_3OD$) $\delta_H$ 8.64 (1H, s), 8.15 (1H, d, J=6.9 Hz), 7.49 (1H, d, J=6.9 Hz), 7.08 (1H, s), 4.17 (1H, dd, J=5.3, 8.6 Hz), 3.85 (3H, s), 3.61 (1H, dd, J=4.9, 7.9 Hz), 3.48 (1H, dd, J=6.9, 12.7 Hz), 3.41 (1H, dd, J=5.8, 12.7 Hz), 3.35 (1H, t, J=7.4 Hz), 3.30 (3H, s), 2.75 (1H, m), 2.60 (1H, J=8.6, 12.1 Hz), 2.52 (1H, J=5.3, 12.1 Hz), 2.41 (1H, m), 2.29 (1H, m), 1.73 (2H, m), 1.66 (2H, m), 1.59 (2H, m), 1.01 (3H, t, J=7.1 Hz), 0.52 (1H, J=8.1 Hz), 0.48 (1H, J=8.1 Hz). $^{13}$C NMR ($CD_3OD$) $\delta_c$ 170.2, 168.4, 161.3, 144.2, 137.8, 130.2, 129.9, 127.4, 125.6, 107.5, 82.1, 68.7, 67.5, 57.1, 56.4, 54.1, 53.4, 52.8, 49.2, 47.8, 37.5, 36.7, 32.5, 27.3, 22.1, 21.3, 9.8. HRESIMS m/z 519.2584 [M+Na]$^+$ (calcd for $C_{27}H_{36}N_4O_5Na^+$, 519.2578) (100%). Anal. Calcd for $C_{27}H_{36}N_4O_5$.HCl: C, 60.84; H, 7.00; Cl, 6.65; N, 10.51. Found: C, 60.91; H, 6.96; Cl, 6.68; N, 10.48.

Formula C (hydrochloride salt): pale yellow needles, melting point 211-212° C.; $[\alpha]_D$ +14.7° (c 0.19, MeOH); $^1$H NMR ($CD_3OD$) $\delta_H$ 8.72 (1H, s), 8.09 (1H, d, J=6.7 Hz), 7.55 (1H, d, J=6.7 Hz), 7.21-7.08 (5H, m), 7.03 (1H, s), 4.21 (1H, dd, J=5.5, 8.3 Hz), 3.87 (3H, s), 3.69 (1H, dd, J=4.7, 7.8 Hz), 3.55 (1H, dd, J=6.6, 12.8 Hz), 3.46 (1H, dd, J=5.7, 12.8 Hz), 3.38 (1H, t, J=7.1 Hz), 3.29 (3H, s), 3.15 (1H, m), 2.89 (2H, m), 2.67 (1H, J=8.3, 12.2 Hz), 2.56 (1H, J=5.5, 12.2 Hz), 2.47 (1H, m), 2.24 (1H, m), 1.76 (2H, m), 1.62 (2H, m), 0.55 (1H, J=7.8 Hz), 0.50 (1H, J=7.8 Hz). $^{13}$C NMR ($CD_3OD$) $\delta_c$ 170.8, 168.1, 162.4, 146.1, 141.5, 138.3, 130.8, 129.7, 128.8, 128.5, 127.9, 126.1, 125.2, 106.9, 81.7, 69.2, 67.1, 59.2, 56.9, 53.8, 53.1, 52.4, 50.6, 49.0, 39.4, 37.9, 36.2, 34.1, 23.3, 21.9. HRESIMS m/z 581.2729 [M+Na]$^+$ (calcd for $C_{32}H_{38}N_4O_5Na^+$, 581.2734) (100%). Anal. Calcd for $C_{32}H_{38}N_4O_5$.HCl: C, 64.58; H, 6.61; Cl, 5.96; N, 9.41. Found: C, 64.61; H, 6.58; Cl, 5.94; N, 9.44.

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Additionally, the compounds of the invention include pharmaceutically acceptable salts, multimeric forms, active metabolites, precursors and salts of such metabolites of the compounds of the present invention.

The compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an .alpha.-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The compound of the present invention are solids, it is understood by those skilled in the art that the compound of the present invention and salts may exist in different crystal or polymorphic forms, all of which are intended to be within the scope of the present invention and specified structural formulas.

The compounds of the present invention in accordance with the present invention are useful in the treatment of malaria and diseases and disorders associated with malaria or a Plasmodium parasite.

Antimalarial Activity and Toxicity

In Vitro Blood Stage Antimalarial Efficacy Evaluation. New compounds were tested against a panel of strains of P. falciparum. The $IC_{50}$ values (50% inhibitory concentrations) were summarized in Table 1. The antimalarial activity of the natural product Formula A was comparable to the positive controls chloroquine and amodiaquine. Derivative compounds Formula B and Formula C exhibited superior and equally potent antimalarial activity against chloroquine sensitive and resistant malaria strains.

parum African NF54 strain or the multi-drug resistant P. falciparum Thailand T24 strain. The data are summarized in Table 3. The antimalarial activities of natural product Formula A was comparable to the positive controls. Derivative compounds Formula B and Formula C exhibited superior antimalarial activity against chloroquine sensitive and resistant malaria strains. The $ED_{50}$'s (the dose leading to 50% parasite growth inhibition compared to the blank control) are smaller than 1.0 mg/kg.

TABLE 3

In Vivo Efficacy Evaluation of Natural Product and Derivative Compounds [$ED_{50}$ (mg/kg)][a]

| Strain | P. berghei NK-65 | P. falciparum NF54 | P. falciparum T24 |
|---|---|---|---|
| Formula A | 2.1 | 3.9 | 4.2 |
| Formula B | 0.13 | 0.24 | 0.27 |
| Formula C | 0.11 | 0.20 | 0.18 |
| Chloroquine | 2.0 | 4.6 | NE[b] |
| Dihydroartemisinin | 0.56 | 1.1 | 1.2 |

[a]Antimalarial activities were determined after oral administration of test compound once daily for 4 days to infected mice.
[b]Not effective.

TABLE 1

In Vitro Antimalarial Activities of New Compounds versus a Panel of P. falciparum Isolates[a] [$IC_{50}$ (nM)]

| Strain | PH3 | 3D7 | DD2 | TM6 | K1 | TM4 | V1S |
|---|---|---|---|---|---|---|---|
| Chloroquine | 33.4 ± 9.1 | 9.7 ± 3.4 | 45.8 ± 10.2 | 96.4 ± 6.9 | 165.6 ± 19.3 | 115.2 ± 12.7 | 152.2 ± 14.1 |
| Amodiaquine | 15.9 ± 3.2 | 4.9 ± 1.8 | 9.1 ± 1.2 | 7.5 ± 2.4 | 21.2 ± 2.1 | 15.2 ± 2.6 | 8.7 ± 2.5 |
| Formula A | 16.1 ± 3.9 | 11.7 ± 4.2 | 14.7 ± 3.2 | 14.9 ± 4.2 | 18.4 ± 5.6 | 35.6 ± 9.4 | 15.1 ± 3.6 |
| Formula B | 0.17 ± 0.04 | 0.19 ± 0.04 | 0.27 ± 0.07 | 0.18 ± 0.03 | 0.22 ± 0.05 | 0.23 ± 0.04 | 0.26 ± 0.05 |
| Formula C | 0.19 ± 0.04 | 0.22 ± 0.05 | 0.16 ± 0.03 | 0.09 ± 0.02 | 0.25 ± 0.04 | 0.31 ± 0.07 | 0.12 ± 0.03 |

[a]PH3, 3D7, and DD2 are all chloroquine sensitive strains of P. falciparum.
The rest of the strains (TM6, K1, TM4, V1S) are chloroquine resistant.

In Vitro Liver-Stage Antimalarial Efficacy Evaluation. Any new desirable antimalarial drug should be broad spectrum: it should be active against both the blood stage and the liver stage of the parasite. New compounds were assessed on the Plasmodium yoelii liver stage in vitro. The liver stage of P. yoelii is a parasite of rodent extensively used as an experimental model for studying the initial phase of the malaria infection. As shown in Table 2, derivative compounds (Formula B and Formula C) have shown excellent effectiveness against liver stage malaria parasites.

TABLE 2

Antimalarial Activity of New Compounds on Liver Stage of P. yoelii yoelii [$IC_{50}$ (nM)]

| Atovaquone | Primaquine | Formula A | Formula B | Formula C |
|---|---|---|---|---|
| 57 | 76 | 62 | 5.8 | 7.1 |

Antimalarial Efficacy and Acute Toxicity Studies in Animal Models

Antimalarial efficacy data was obtained by evaluating new compounds in two rodent models: (I) Swiss mice infected with rodent malaria strain P. berghei; (II) Immunocompromised BXN mice infected with either the sensitive P. falci- The acute toxicity study of test compounds (Formula A, Formula B, and Formula C) was conducted with Sprague-Dawley rats following intragastric administration. After administration, all rats were observed for 2 weeks. The data are summarized in Table 4. Based on the acute toxicity data, the MTDs (maximum tolerated dose) were determined to be greater than 500 mg/kg and the NOAEL (no observable adverse effect level) is greater than 100 mg/kg/day. Antimalarial potency was measured by determination of the MCD (minimum clearance dose), a commonly used efficacy measurement. The primary therapeutic indices, which were obtained by using the MCDs as the effective parameters, were calculated. A secondary therapeutic indices measure of antimalarial potency was determined by use of the dose for the MCureD (minimum curative dose). Based on the therapeutic index data, all new compounds are much less toxic than existing antimalarial drugs (chloroquine, mefloquine and artemisinin derivatives) and are expected to possess wide therapeutic windows.

TABLE 4

Therapeutic indices, MCDs, MCureDs, and MTDs of New Compounds.[a]

| Efficacy Parameter | Formula A | Formula B | Formula C | Chloroquine | Mefloquine | Artesunate[b] |
|---|---|---|---|---|---|---|
| MCD [mg/kg] | 8.25 | 3.16 | 2.45 | 60.0 | 9.95 | 6.75 |
| MCureD [mg/kg] | 32.1 | 14.2 | 9.82 | None | 40.5 | 25.4 |
| MTD [mg/kg] | 560 | 750 | 710 | 240 | 600 | 250 |
| Primary therapeutic index[c] | 68 | 237 | 290 | 4 | 60 | 37 |
| Secondary therapeutic index[d] | 17 | 53 | 72 | None | 15 | 10 |

[a]Five to seven rats were included in each group. The strain is rodent *P. berghei*.
[b]Route of administration for Artesunate is iv. All others were administered orally.
[c]Primary therapeutic indices were calculated as MTD divided by MCD.
[d]Secondary therapeutic indices were calculated as MTD divided by MCureD.

Derivative compounds were also tested for oral prophylactic activity. Mice treated with a single dose of 0.5 mg/kg of Formula B or Formula C within the period of 2 days pre-infection through 2 days post-infection were completely protected from malaria. Data were summarized in Table 5 and Table 6.

TABLE 5

Prophylactic Anti-Malarial Activity of Formula B.
Mice infected and treated/Mice surviving day 60

| | dose, mg/kg | | | |
|---|---|---|---|---|
| Day of Treatment | 0.5 | 2 | 8 | 32 |
| −2 | 5/5 | 5/5 | 5/5 | 5/5 |
| −1 | 5/5 | 5/5 | 5/5 | 5/5 |
| 1 | 5/5 | 5/5 | 5/5 | 5/5 |
| 2 | 5/5 | 5/5 | 5/5 | 5/5 |
| Controls | 0/5 | | | |

TABLE 6

Prophylactic Anti-Malarial Activity of Formula C.
Mice infected and treated/Mice surviving day 60

| | dose, mg/kg | | | |
|---|---|---|---|---|
| Day of Treatment | 0.5 | 2 | 8 | 32 |
| −2 | 5/5 | 5/5 | 5/5 | 5/5 |
| −1 | 5/5 | 5/5 | 5/5 | 5/5 |
| 1 | 5/5 | 5/5 | 5/5 | 5/5 |
| 2 | 5/5 | 5/5 | 5/5 | 5/5 |
| Controls | 0/5 | | | |

In Vivo Efficacy Studies in Aotus Monkey Model. The monkeys selected for the study had active infections of the chloroquine-resistant FVO strain of *P. falciparum*. Once parasitemias reached 5,000/μl (or as deemed appropriate by the attending veterinarian), they were treated orally with Formula B or Formula C at 2, 4, 8, or 16 mg/kg/day for 3 days. For compound Formula B, the dosage needed to cure 50% of animals was 4 mg/kg/day and the dosage needed to cure 100% of animals was 16 mg/kg/day. For compound Formula C, the 50% curative dose was 2 mg/kg/day and the 100% curative dose was 8 mg/kg/day (Table 7).

TABLE 7

Efficacy of Test Compounds Against Blood Stages of *P. falciparum* in Aotus Monkeys

| Test compounds | Dose (mg/kg/day)[a] | Cure rate (%)[b] |
|---|---|---|
| Formula B | 2 | 1/4 (25) |
| | 4 | 5/7 (71) |
| | 8 | 4/5 (80) |
| | 16 | 5/5 (100) |
| Formula C | 2 | 2/4 (50) |
| | 4 | 4/6 (67) |
| | 8 | 5/5 (100) |
| | 16 | 5/5 (100) |

[a]*P. falcipanum*-infected Aotus monkeys were administered drug orally once a day for 3 days beginning the day after a parasitemia level of approximately 5,000 organisms per mm³ was reached.
[b]Number of animals cured/total number tested (cure is defined as clearance of parasitemia with no recrudescence).

Causal Prophylactic and Radical Curative Test in Rhesus Monkeys. The causal prophylactic and radical curative antimalarial activity of the new compounds Formula B and Formula C was assessed in a *Plasmodium cynomolgi* sporozoite-challenged Rhesus monkey model. Assessment of radical curative activity of the test compounds was carried out using the monkeys' developed parasitemia during the causal prophylactic experiments when the test compounds showed no or weak activity. The results are summarized in Table 8 and Table 9.

TABLE 8

Causal Prophylactic Activity of Compounds in *P. Cynomolgi* Sporozoite-Challenged Rhesus Monkeys (Route: PO)

| Monkey group #[a] | Compound | Dose (mg/kg) | Days treated | Parasite patency (days postinoculation) |
|---|---|---|---|---|
| 1 | Control | N/A | N/A | 8 days |
| | | | | 8 days |
| 2 | Formula B | 15 | 1 daily for 3 days | 41 days |
| | | | | 55 days |
| 3 | Formula C | 15 | 1 daily for 3 days | 48 days |
| | | | | 64 days |

[a]Two monkeys per dose group.

TABLE 9

Radical Curative Activity of Compounds in Relapsed Rhesus Monkeys (Route: PO)

| Group No.[a] | Drug 1 | Drug 2 | Dose (mg/kg)[b] | # Doses per day[b] | Results | Days post-treatment |
|---|---|---|---|---|---|---|
| 1 | CQ[c] | None | N/A | N/A | relapse | 9 days |
|   |   |   |   |   |   | 9 days |
| 2 | CQ | Formula B | 15 | 1 daily for 3 days | delayed relapse | 42 days |
|   |   |   |   |   | radical curative | no relapse |
| 3 | CQ | Formula C | 15 | 1 daily for 3 days | delayed relapse | 53 days |
|   |   |   |   |   | radical curative | no relapse |
| 4 | CQ | Formula B | 30 | 1 daily for 3 days | radical curative | no relapse |
|   |   |   |   |   | radical curative | no relapse |
| 5 | CQ | Formula C | 30 | 1 daily for 3 days | radical curative | no relapse |
|   |   |   |   |   | radical curative | no relapse |

[a]Two monkeys per dose group.
[b]Dose and number of doses are for drug 2.
[c]Chloroquine was used at 10 mg/kg/day for 7 days.

Results indicated that both compounds delayed patency of treated monkeys more than a month as compared with the untreated control monkeys. Monkeys which developed parasitemia in the causal prophylactic test were used for the radical curative test. Test compounds were co-administered with chloroquine to eliminate the blood stage parasites. At the 15 mg/kg/day level, one out of two monkeys that were treated either with Formula B or Formula C was cured. Other treated monkeys showed a delay in relapse from 42 to 53 days, as compared to 9 days for untreated control animals. At the 30 mg/kg/day level, all monkeys that were treated either with Formula B or Formula C were cured.

The present invention, hence, relates to the finding that some new natural product derivative compounds (Formula B and Formula C) have significantly greater activity and less toxicity in the treatment of malaria. The present invention relates to new chemical compositions and also to the use of these compositions as pharmaceuticals when combined with an acceptable pharmaceutical carrier in the treatment of malaria.

Administration of the compounds of the invention may be parenteral, oral, intravenous, intramuscular, subcutaneous, intrapleural, intrathecal, intraperitoneal, aerosol or transdermal administration to achieve the desirable antimalarial effect. These drugs may be administered as the free base form or in the form of a pharmaceutically acceptable acid addition salt wherein the acid addition salt may be either organic or inorganic in nature. Suitable inorganic acids for salt formation include but are not restricted to: phosphoric acid, hydrochloric acid or sulfuric acid. Suitable organic acids for the formation of salts may include but are not restricted to: succinic acid, citric acid, fumaric acid or isothionic acid. When administered orally, the compounds of the invention may be in the form of tablets (single or multilayer, coated or uncoated) capsules or dragees. These oral formulations may be admixed with a solid excipient such as lactose, sucrose, starch, microcrystalline cellulose, magnesium sterate, or talc. When parenteral administration may be indicated, an aqueous solution or an oleaginous formulation of the agent may be employed. Aqueous solutions can be prepared in water or physiological saline, either with or without buffers. Oleaginous formulation may be made in natural oils such as peanut oil or olive oil, for example. The actual dosage amount administered can be determined by physical and physiological factors such as body weight, severity of condition, and idiopathy of the subject.

Biological Testing Procedures

In Vitro Anti-Malarial Activity Evaluation.

Test compounds were initially dissolved in DMSO and diluted 400 fold in RPMI 1640 culture medium supplemented with 25 mM Hepes, 32 mM $NaHCO_3$ and 10% Albumax I (Gibco, NY). These solutions were subsequently serially diluted two-fold with a Beckman Biomek® 1000 Robot (Fullerton, Calif.) over 11 different concentrations. The parasites were exposed to serial dilutions of each compound for 48 hrs and incubated at 37° C. with 5% $O_2$, 5% $CO_2$ and 90% $N_2$ prior to the addition of [$^3$H]hypoxanthine. After a further incubation of 18 hrs, parasite DNA was harvested from each microtiter well using Packard Filtermate™ 196 Harvester (Meriden, Conn.) onto glass filters. Uptake of [$^3$H]hypoxanthine was measured with a Packard TopCount Liquid Scintillation Counter (Packard Instrument Co.). Concentration-response data was analyzed using a non-linear regression logistic dose response model and the $IC_{50}$ values (50% inhibitory concentrations) for each compound were calculated.

Blood Schizontocidal Test in Rodent Models

Drugs were mixed in 0.5% hydroxycellulose 0.1% Tween 80 and administered orally on days 3, 4 and 5 post-infection. CD-1 male or female mice, 5 weeks of age, were infected with 5.times.10.sup.4 parasitized erythrocytes of *Plasmodium berghei* KBG strain. Blood films were taken on day +6 and weekly thereafter until day +60. Parasitemias were calculated. Mortality data was tabulated for 60 days at which time all mice surviving that were blood film negative were considered cured.

Compounds were tested at three dose levels, 4, 1, and 0.25 mg/kg body weight per day. The activity of these compounds were compared with the untreated control. In untreated controls, death occurs within 8-9 days. Compounds which are effective against *Plasmodium berghei* infection increase the mean survival time of the infected animals when compared with the untreated controls. Mice that survive after thirty days and are free of parasites in blood are considered cured.

Efficacy of the drug is determined by the number of cures at the end of a 30 day period and the increase in mean survival time over the control. The effect of the test drugs also could be determined by the reduction of the parasitemia (percentage of the red blood cells detected with the parasites) over the untreated control on day 6, one day after the treatment is completed. Both these methods yield virtually identical results. If the dose of test compounds are inadequate, after initial clearance, residual parasites will multiply and relapses will occur within thirty days.

Prophylactic Test in Rodent Models

Drugs were mixed in 0.5% hydroxycellulose 0.1% Tween 80 and administered orally b.i.d. either on day 5, 4, 3, 2, or 1 prior to the infection or 1 or 2 days postinfection. CD-I male or female mice, 5 weeks of age, were infected with 5.times.10.sup.4 parasitized erythrocytes of *Plasmodium berghei* strain. Blood films were taken on day +6 and weekly thereafter until day+30. Mortality data was tabulated for 30 days at which time all mice surviving that were blood film negative were considered cured.

Efficacy of Test Compounds Against Blood Stages of *P. falciparum* in Aotus Monkeys.

Malaria-naive Panamanian owl monkeys (*Aotus lemurinus lemurinus*) were used as hosts for chioroquine-resistant *P. falciparum*. The chloroquine-resistant Vietnam Smith strain was used in the initial experiments. In subsequent studies, a recrudescent isolate from a Vietnam Smith strain infected Aotus monkey treated with chloroquine was used. This strain, designated Vietnam Smith/RE, was more resistant to chloroquine as evidenced by limited effects on parasitemia in Aotus monkeys receiving 20 mg/kg/day of chloroquine for seven days.

Each monkey was inoculated intravenously with $5 \times 10^6$ trophozoites of the chloroquine resistant Vietnam Smith or Vietnam Smith/RE strain of *P. falciparum*. The inoculum size produced a parasitemia of at least $5 \times 10^3/mm^3$ by the fifth day postinoculation, at which time treatment was begun. Stock solutions of water-soluble drug were prepared at appropriate concentrations and maintained at 4° C. during the course of treatment. A suspension of water-insoluble drugs was prepared in 0.3% methylcellulose just prior to use. All drugs were administered by gastric intubation in a volume of 7.0 ml, followed by a 7.0-mi rinse with either water or 0.3% methylcellulose. Test drug was given orally for either three or seven consecutive days. In several experiments, the putative resistance modulator was given three times per day (8:00 AM, noon, and 4:00 PM) for three or seven days.

Giemsa-stained blood smears were prepared from all animals and examined daily beginning the day after inoculation until parasitemia was cleared and for at least seven days thereafter. At that time, blood films were examined twice a week up to 100 days after treatment. Thick blood films were considered negative if no parasites were seen after examination for at least five min. Ten or less parasites on a thick blood film were recorded as <10. Parasitemia was enumerated and expressed as number of parasites/mm³. Treated animals were observed twice a day for signs of drug toxicity, as evidenced by abnormal behavior, anorexia, diarrhea, or vomiting. Necropsies were per formed on all animals that died. In conducting the research described in this report, the investigators adhered to the Guide for the Care and Use of Laboratory Animals, as promulgated by the National Research Council.

The outcome of each infection was compared with untreated controls and monkeys treated with chloroquine. The infection was considered suppressed when parasitemia persisted throughout treatment, but was reduced to less than one-fiftieth the level of parasitemia in the control on the same day postinitiation of treatment. An infection was considered cleared if the parasitemia became negative by 12 days after the infection became patent and remained negative for seven days; clearance of parasitemia after the infection was patent for 12 days was indicative of a self-limiting infection and was not attributed to a drug affect. An infection was considered cured if the parasitemia cleared and blood films remained negative for 100 days after the end of treatment. Infections that failed to be cured by the initial treatment were subsequently treated with higher doses of resistance modulator plus chloroquine or with mefioquine. Re-treatment data were not considered in the analysis of drug efficacy because of the high rate of self-limiting infections observed in this model.

Causal Prophylactic Activity of Compounds in *P. Cynomolgi* Sporozoite-Challenged Rhesus Monkeys.

Two monkeys were used in each test group. The control animals developed parasitemia in about 10 days after inoculation of about $1 \times 10^6$ *P. cynomolgi* sporozoites harvested from *Anopheles dirus*. All the monkeys received three treatments, once a day for three consecutive days beginning a day before (−1, 0,+1) the sporozoites challenge. The control monkeys (group 1) received HECT and the experimental animals received testing compound by using 8 Fr., 15-in. long nasogastric tubes.

Radical Curative Activity of Compounds in Relapsed Rhesus Monkeys.

Assessment of radical curative activity of the test compounds was carried out using the monkeys' developed parasitemia during the causal prophylactic experiments when the test compounds showed no or weak activity. Monkeys were treated with chloroquine (10 mg/kg/day) orally for 7 consecutive days, and the test compounds by PO for 3 consecutive days after the parasitemia level reached 5,000 parasites/mm³. Chloroquine at 10 mg/kg/day×7 days eliminated the blood stage parasites but not the liver stage hypnozoites. Compounds with antihypnozoite activity will delay the relapse or radically cure the infection. To evaluate the radical curative properties, daily blood samples were followed for 21 days, 3 times per week for 4 weeks, and then 2 times weekly until 100 days after the last day of test compound administration. Parasite clearance should occur in all animals treated with chloroquine. Relapse was expected in the control group. Relapse in the treated group indicates failure of the test compounds. Monkeys that showed no relapse after 100 days were considered radically cured. Relapses of the control monkeys were treated with chloroquine once daily for 7 days, and they were observed for the second relapse. Relapse in experimental animals and the second relapse of the control monkeys were treated with the standard 7 day oral CQ and primaquine (1.78 mg base/kg). After standard treatment, blood smears were monitored daily for 4 consecutive days of negative results and 2 times weekly for 2 weeks.

Unless defined otherwise, all technical and scientific terms used herein have the same meaning as commonly understood by one of ordinary skill in the art to which this invention belongs. Although any methods and materials similar or equivalent to those described can be used in the practice of testing of the present invention, the preferred methods and materials are described herein.

It is understood that the examples and embodiments described herein are for illustrative purposes only and the various modifications or changes in light thereof will be suggested to persons skilled in the art and are to be included within the spirit and purview of this application and scope of the appended claims.

What is claimed is:

1. A method for the treatment of malaria comprising administering to a subject a therapeutically effective amount of a compound having the Formula B:

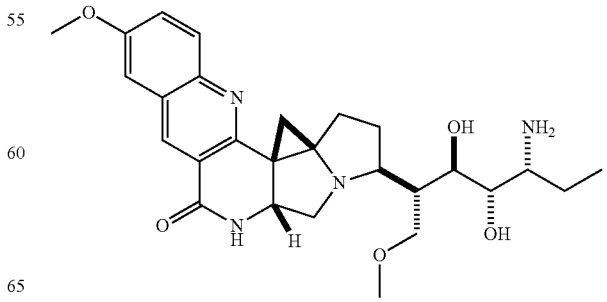

Formula B

Or a compound having the Formula C:
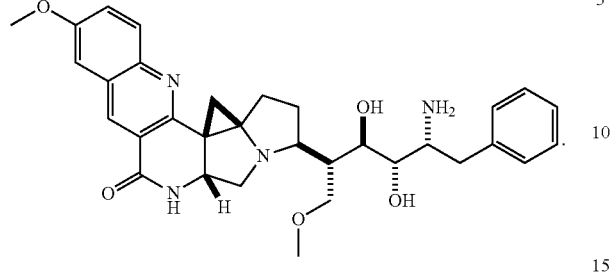
Formula C
* * * * *